United States Patent [19]

Kuusela et al.

[11] Patent Number: 5,776,712

[45] Date of Patent: Jul. 7, 1998

[54] **METHODS AND MATERIALS FOR THE DETECTION OF *STAPHYLOCOCCUS AUREUS***

[75] Inventors: Pentti Kuusela; Pekka Hildèn, both of Helsinki, Finland

[73] Assignee: Helsinki University Licensing, Ltd., Helsinki, Finland

[*] Notice: The term of this patent shall not extend beyond the expiration date of Pat. No. 5,496,706.

[21] Appl. No.: 610,389

[22] Filed: Mar. 4, 1996

Related U.S. Application Data

[63] Continuation-in-part of Ser. No. 169,524, Dec. 17, 1993, Pat. No. 5,496,706.

[51] Int. Cl.$^6$ .................... G01N 33/569; G01N 33/536; G01N 33/577
[52] U.S. Cl. .................... 435/7.33; 424/243.1; 530/387; 530/388.4; 530/389.5; 435/7.32; 436/547
[58] Field of Search .................... 530/387.1, 388.4, 530/389.5; 424/243.1; 435/7.33, 7.32; 436/547

[56] References Cited

U.S. PATENT DOCUMENTS 5,496,706  3/1996  Kuusela et al. .................... 435/7.33

FOREIGN PATENT DOCUMENTS

| A 05 339 289 | 12/1993 | Japan . |
| 89/02077 | 3/1989 | WIPO . |
| WO 89/02077 | 3/1989 | WIPO . |
| WO 95/16915 | 6/1995 | WIPO . |

OTHER PUBLICATIONS

Kuusela et al. "Rapid Detection of Methicillin–Resistant *Staphylcoccus aureus* Strains Not Identified by Side Agglutination Tests", J. Clin. Microbiol., 32(1):143–147 (Jun. 1994).

Aldridge et al., "Comparison of Rapid Identification Assays for *Staphylococcus aureus*," *J. Clin. Microbiol.*, 19(5):703–704 (May, 1984).

Baker et al., "Evaluation of Various Rapid Agglutination Methods for the Identification of *Staphylococcus aureus*," *J. Clin. Microbiol.*, 21(5):726–729 (May, 1985).

Berger–Bächi et al., "FemA a Host–Mediated Factor Essential for Methicillin Resistance in *Staphylococcus aureus*: Molecular Cloning and Characterization," *Mol. Gen. Genet.*, 219:263–269 (1989).

Berke et al., "Evaluation of Rapid Coagulase Methods for the Identification of *Staphylococcus aureus*," *J. Clin. Microbiol.*, 23(5):916–919 (May, 1986).

Blair et al., "Phage Typing of Staphylococci," *Bull. Wld. Hlth. Org.*, 2:771–784 (1961).

Brown, W.J., Comparison of a Yellow Latex Reagent with Other Agglutination Methods for the Identification of *Staphylococcus aureus, J. Clin. Microbiol.*, 23(3):640–642 (Mar., 1986).

Eskola et al., "A Randomized, Prospective Field Trail of a Conjugate Vaccine in the Protection of Infants and Young Children Against Invasive *Haemophilus Influenzae* Type b Disease," *N. Engl. J. Med.*, 323(20):1381–1387 (1990).

Essers et al.,"Rapid and Reliable Identification of *Staphylococcus aureus* by a Latex Agglutination Test," *J. Clin. Microbiol.*, 12(5):641–643 (Nov., 1980).

Fournier et al., "New Latex Reagent Using Monoclonal Antibodies to Capsular Polysaccharide for Reliable Identification of Both Oxacillin–Susceptible and Oxacillin–Resistant *Staphylococcus aureus*," *J. Clin. Microbiol.*, 31(5):1342–1344 (May, 1993).

Guzmàn et al., "Novel Immunoenzymatic Assay for Identification of Coagulase and Protein A–Negative *Staphylococcus aureus* Strains," *J. Clin. Microbiol.*, 30(5):1194–1197 (May, 1992).

Kloos et al., "*Staphylococcus*," Manual of Clinical Microbiology, Chapter 28, Balows et al. (eds.), pp. 222–237 (1991).

Kuusela, P., "Fibronectin Binds to *Staphylococcus aureus*," *Nature*, 276:718–720 (Dec. 14, 1978).

Kuusela & Saksela, "Binding and Activation of Plasminogen at the Surface of Staphylococcus aureus: Increase in Affinity After Conversion to the Lys Form of the Ligand," *Eur. J. Biochem.*, 193;759–765 (1990).

Kuusela et al., "Rapid Detection of Methicillin–Resistant Staphylococcus aureus Strains Not Identified by Slide Agglutination Tests," *J. Clin. Microbiol.*, 32(1):143–147 (Jan., 1994).

Kuusela et al., "Tissue–Type Plasminogen Activator–Mediated Activation of Plasminogen on the Surface of Group A, C, and G Streptococci." *Infect. Immun.*, 60(1):196–201 (Jan., 1992).

Laemmli, U.K., "Cleavage of Structural Proteins During the Assembly of the Head of Bacteriophage T4." *Nature*, 227:680–685 (Aug. 15, 1970).

Lairscey et al., "Performance of Four Slide Agglutination Methods for Identification of *Staphylococcus aureus* When Testing Methicillin–Resistant Staphylococci." *J. Clin. Microbiol.*, 25(1):181–182 (Jan., 1987).

Lopes et al., "Presence of Laminin Receptors in *Staphylococcus aureus,*" *Science*, 229:275–277 (Jul. 19, 1985).

Lowrey et al., "Protein Measurement With the Folin Phenol Reagent." *J. Biol. Chem.*, 193:265–275 (1951).

(List continued on next page.)

*Primary Examiner*—James C. Housel
*Assistant Examiner*—Jennifer Shaver
*Attorney, Agent, or Firm*—Marshall, O'Toole, Gerstein, Murray & Borun

[57] ABSTRACT

The present application discloses a novel method for the detection of *Staphylococcus aureus* and methicillin-resistant strains of *Staphylococcus aureus*. Further disclosed is an approximately 230 kDa protein and the use of such protein in detection assays for *Staphylococcus aureus* and in other diagnostic and therapeutic applications. Also disclosed are methods of purifying the protein and biologically active fragments thereof.

10 Claims, 3 Drawing Sheets

OTHER PUBLICATIONS

Niskanen et al., "Evaluation of Three Slide Agglutination Tests for Rapid Identification of *Staphylococcus aureus*," *Acta vet scand.* 32:543–549 (1991).

Piper et al., "Efficacies of Rapid Agglutination Tests for Identification of Methicillin–Resistant Staphylococcal Strains as *Staphylcoccus aureus*," *J. Clin. Microbiol.*, 26(9):1907–1909 (Sep., 1988).

Ruane et al., "Failure of Rapid Agglutination Methods to Detect Oxacillin–Resistant *Staphylcoccus aureus*," *J. Clin. Microbiol.*, 24(3):490–492 (Sep., 1986).

Schindler & Schuhardt, "Lysostaphin: A New Bacteriolytic Agent for the Staphylococcus," *Proc. Nat'l Acad. Sci., USA*, 51:414–421 (1964).

Schneewind et al., "Structure of the Cell Wall Anchor of Surface Proteins in *Staphylococcus aureus*," *Science*, 268:103–106 (Apr. 7, 1995).

Speziale et al., "Binding of Collagen to *Staphylococcus aureus* Cowan 1," *J. Bacteriol.*, 167(1):77–81 (Jul., 1986).

Towbin et al., "Electrophoresis Transfer of Proteins From Polyacrylamide Gels to Nitrocellulose Sheets: Procedure and Some Applications," *Proc. Nat'l Acad. Sci., USA*, 76(9):4350–4354 (Sep., 1979).

Ubukata et al., "Occurrence of a β–Lactam–Inducible Penicillin–Binding Protein in Methicillin–Resistant Staphylococci," *Antimicrobial Agents and Chemotherapy*, 27(5):851–857 (May, 1985).

Wanger et al., "Latex Agglutination–Negative Methicillin–Resistant *Staphylococcus aureus* Recovered from Neonates: Epidemiologic Features and Comparison of Typing Methods," *J. Clin. Microbiol.*, 30(10):2583–2588 (Oct., 1992).

Woolfrey et al., "An Evaluation of Three Rapid Coagglutination Tests: Sero–STAT©, Accu–Staph™ and Staphyloslide™, for Differentiating Staphylococcus aureus From Other Species of Staphylococci," *Am. J. Clin. Pathol.*, 81(3):345–348 (1984).

METHODS AND MATERIALS FOR THE DETECTION OF STAPHYLOCOCCUS AUREUS

The present application is a continuation-in-part of U.S. patent application Ser. No. 08/169,524, filed Dec. 17, 1993 U.S. Pat. No. 5,496,706.

FIELD OF THE INVENTION

The present invention generally relates to methods for the detection of the bacterium, Staphylococcus aureus, and materials related thereto, including a purified S. aureus surface protein; a purified and isolated nucleic acid encoding the protein; antibody substances which specifically bind to the protein; and compositions and formulations comprising such materials.

BACKGROUND OF THE INVENTION

Staphylococcus aureus is a gram-positive facultative aerobe which is considered among the most virulent species of the genus Staphylococcus. It is part of the bacterial flora indigenous to humans. A Staphylococcus aureus infection may result when injury occurs to the skin or protective mucous membranes, thus allowing invasion of the bacterium. Epidermal infection is the most common form of Staphylococcus infection in humans. However, Staphylococcus aureus is also a common organism isolated from patients with nosocomial pneumonia.

When introduced in food, Staphylococcus aureus may produce one or more staphylococcal enterotoxins. If ingested, heat-stable Staphylococcal enterotoxins may produce symptoms of food poisoning and a range of other diseases.

Staphylococcus aureus possesses a resistant cell wall which comprises a cross-linked peptidoglycan layer which may protect the cell from invasion by the host. In addition, the cell wall is resistant to phagocytosis which is thought to be due, in part, to the production of Protein A on the cell surface. Staphylococcus aureus also produces hemolytic toxin which may damage blood cells and immune cells.

Treatment of Staphylococcus aureus infections generally comprises the use of erythromycin, cephalosporins, or methicillin. However, numerous strains have emerged which are resistant to methicillin. These methicillin-resistant strains are usually resistant to most other anti-microbial drugs, and therapy in response to a methicillin resistant strain usually requires administration of a more potent antibiotic, such as vancomycin.

Of interest to the field as well as to the present invention, are laboratory tests to identify Staphylococcus aureus infection and, in particular, methicillin-resistant strains which may not be detected by traditional assays and may be unresponsive to traditional therapy. Assays for Staphylococcus aureus typically are based upon (1) a coagulation assay, measuring coagulation of test plasma; (2) observation of the morphology of the suspected pathogen; (3) detection of the production of thermostable nucleases; and (4) the utilization by the pathogen of specific sugars as carbohydrate sources. Kloos, et al., Manual of Clinical Microbiology, 5th Edition, American Society for Microbiology, Washington, D.C., pp. 222–237 (Balows, et al., eds. 1991). Such traditional methods suffer from serious drawbacks. Traditional assays for S. aureus require several hours of incubation and may provide ambiguous results. Slide agglutination assays have been developed which may overcome some of those problems. See, e.g., Aldridge, et al., J. Clin. Microbiol., 19: 703–704 (1984); Baker et al., J. Clin. Microbiol., 21: 726–729 (1985); Berke and Tilton, J. Clin. Microbiol., 23(5): 916–919 ((1986); Brown, J. Clin. Microbiol., 23(3): 640–642 (1986); Essers and Radebold, J. Clin. Microbiol., 12(5): 641–643 (1980); Woolfrey et al., Am J. Clin. Pathol., 81(3): 345–348 (1984); Berger-Bachi, et al., Mol. Gen. Genetics, 219: 263–269 (1989). Such assays involve particles coated with fibrinogen or fibrinogen and an IgG immunoglobulin. Fibrinogen-binding protein (clumping factor) and protein A, both associated with the cell surface of S. aureus, bind to the coated particles, resulting in a positive assay. However, reports indicate that most such assays are not capable of detecting certain methicillin-resistant S. aureus. Berke and Tilton, supra; Berger-Bachi, supra; Laircsey, et al., J. Clin. Microbiol., 25: 181–182 (1987); Piper, et al., J. Clin. Microbiol., 26: 1907–1909 (1988); Ruane et al., J. Clin. Microbiol., 24(3): 490–492 (1986); Wagner, et al., J. Clin. Microbiol., 30: 2583–2588 (1992).

Failure to detect methicillin-resistant strains may result in misdiagnosis and/or improper therapy. Also, to control the spread of S. aureus-related diseases and to determine the source of an outbreak of S. aureus infection, proper and precise identification of the bacterium, including the strain, is essential.

Accordingly, a need exists for identifiable surface markers for methicillin-resistant strains of S. aureus, to permit rapid detection of such strains and to permit production of vaccines to such strains.

Similarly, there is a need in the art for rapid, reliable means for detecting all methicillin-resistant strains of Staphylococcus aureus, as provided in the present invention.

SUMMARY OF THE INVENTION

The present invention provides an approximately 230 kDa protein, designated MRSA-230, which is isolated from lysostaphin digests of methicillin-resistant Staphylococcus aureus which test negative in standard S. aureus agglutination assays. Thus, the invention includes a purified and isolated MRSA-230 protein, or biologically-active fragment, thereof. The skilled artisan recognizes that biologically active fragments of MRSA-230 are those which retain sufficient biological properties of MRSA-230 to elicit an anti-MRSA-230 immune response, or to be effective in a vaccine against S. aureus. Proteins according to the invention, MRSA-230 and fragments, are useful in generating an immune response directed against S. aureus. More particularly, purified and isolated MRSA-230 protein, or biologically active fragments thereof, are useful for, e.g., generating anti-MRSA-230 antibodies or antisera. For example, a composition or formulation comprising MRSA-230 protein, or biologically active fragments thereof, may be administered to a non-human host to effect production of anti-MRSA-230 antisera, from which anti-MRSA-230 antibodies optionally can be purified. Purified MRSA-230 protein, or biologically active fragments thereof, can be used in vitro to affinity purify anti-MRSA-230 antibodies using techniques known in the art. For therapeutic or prophylactic purposes a composition or formulation comprising MRSA-230 protein, or biologically active fragments thereof, also may be administered to a human host, to effect production of anti-MRSA-230 antibodies in the host.

Thus, an aspect of the invention includes a composition comprising an MRSA-230 protein or biologically active fragment thereof. A pharmaceutical composition according to the invention comprises an MRSA-230 protein or fragment thereof in a pharmaceutically-acceptable carrier. A pharmaceutical composition of the invention comprises an MRSA-230 protein or biologically active fragment thereof in a pharmaceutically acceptable diluent or adjuvent. Such compositions are useful for generating an immune response directed against *S. aureus* and against MRSA-230 in particular. In another embodiment, a composition of the invention includes purified MRSA-230 covalently bound to a solid support or matrix using procedures well-known in the art, such a composition being useful for the affinity purification of anti-MRSA-230 antibodies using well-known techniques.

In another aspect, the invention includes antibody substances that specifically bind to MRSA-230. Anti-MRSA-230 antibodies or antisera comprising the antibodies are useful, inter alia, in methods for the detection of *Staphylococcus aureus* generally and are especially useful for detection of methicillin-resistant strains of *Staphylococcus aureus* which are not detected by standard slide agglutination assays. The MRSA-230 protein, or fragments of that protein which retain MRSA-230 biological activity, are also useful in vaccine compositions which promote an immune response to MRSA-230 and, thus, to *Staphylococcus aureus*.

Detection of *S. aureus* according to the present invention is accomplished using a sample suspected of containing *S. aureus* obtained from any source including, but not limited to, blood, tissue, ascites, pus, urine, and feces. Samples may also be obtained for detection from food; from surfaces, such as floors, tables, and the like; and from airborne particles, such as pollen and dust.

Accordingly, the present application provides a method for the detection of *S. aureus*, comprising the steps of exposing one or more samples suspected of containing an *S. aureus* to a composition comprising anti-MRSA-230 antibodies; and selecting samples which form agglutination products with said antibodies.

In a preferred embodiment of the invention, anti-MRSA-230 antibodies are obtained from immunized rabbit serum by methods known to one of ordinary skill in the art. Also in a preferred embodiment, the sample suspected of containing *S. aureus* is blood, pus, or ascites.

A *Staphylococcus aureus* to be detected by the methods of the present invention may be a methicillin-resistant strain of *S. aureus* or may be resistant to another antimicrobial drug, or combination of antimicrobial drugs.

Anti-MRSA-230 antibodies may be either monoclonal antibodies or polyclonal antibodies produced by well-known methods in the art. See, e.g., Harlow, et al., *Antibodies A Laboratory Manual* (Cold Spring Harbor Laboratory Press, 1988). In one preferred embodiment, the invention includes polyclonal antisera derived from an animal (e.g., rabbit or mouse) following immunization of the animal with methicillin resistant *S. aureus* bacteria (preferably killed bacteria or cell membrane fractions thereof) that are non-agglutinating in standard *S. aureus* detection assays and that express MRSA-230 protein. In another preferred embodiment, the invention includes polyclonal antibodies derived from an animal following immunization with purified MRSA-230 protein or biologically active fragments thereof. In yet another embodiment, the invention includes purified antibodies (polyclonal or monoclonal) which specifically bind MRSA-230 protein.

A kit according to the present invention contains a formulation of anti-MRSA-230 antibody to be applied to a sample suspected of containing *S. aureus* or a methicillin-resistant *S. aureus*.

Antibodies of the invention are useful as inhibitors of reactions mediated by *S. aureus* and as components of *S. aureus* detection methods.

The invention further provides methods for purifying an MRSA-230 protein or biologically active fragments thereof. Such methods include a multi-step chromatographic purification procedure set forth in detail below, and an affinity purification procedure wherein plant lectins are employed. A preferred method for purifying an MRSA-230 protein or biologically active fragment thereof includes the steps of:

(a) obtaining a biological sample containing an MRSA-230 protein or biologically active fragment thereof;

(b) contacting the biological sample with a plant lectin capable of specifically binding to the MRSA-230 protein or biologically active fragment thereof, to form a lectin-MRSA-230 complex;

(c) separating impurities from the complex to yield a purified lectin-MRSA-230 complex; and (d) separating the MRSA-230 protein or biologically active fragment thereof from the plant lectin.

A preferred biological sample from which to purify MRSA-230 protein or fragments is derived from a lysostaphin digest of *Staphylococcus aureus*. Lysostaphin is an enzyme known to specifically cleave the pentaglycine bridge which crosslinks *S. aureus* surface proteins to the *S. aureus* peptidoglycan layer, thereby permitting solubilization/suspension of such surface proteins. See Schindler & Schuhardt, *Proc. Natl. Acad. Sci. USA*, 51: 414–421 (1964). Using binding assays known in the art and/or described herein, suitable plant lectins (those having a binding affinity for MRSA-230 protein or fragments) for use in the foregoing method are identified by routine screening. A preferred plant lectin of step (b) is wheat germ agglutinin (WGA). As set forth herein, practice of the method is facilitated wherein the plant lectin of step (b) is covalently attached to a particle using well-known techniques. In a preferred embodiment, the WGA plant lectin attached to a particle is commercially-available WGA-Sepharose.

Additional aspects of the invention will become apparent to the skilled artisan upon consideration of the detailed description which follows.

DETAILED DESCRIPTION OF THE INVENTION

The present invention relates to methods for detection of *Staphylococcus aureus*, and particularly to detection of methicillin-resistant *Staphylococcus aureus* which are not detected by standard agglutination assays, and to the use of an approximately 230 kDa protein, or biologically-active fragment thereof, in methods for detection of *S. aureus* and in vaccines and pharmaceuticals for the prevention of *S. aureus* and diseases caused by *S. aureus*. Methods according to the invention provide a rapid, accurate, and more complete means for detecting and identifying *S. aureus*, and especially a method of detecting all methicillin-resistant *S. aureus*, than are found in the art. In the present application, strains of *S. aureus* which are negative in standard agglutination tests (i.e., tests designed to detect the surface-associated protein A and/or clumping factor) are referred to as "MRSA-aggl⁻", including methicillin-resistant strains which test negative in standard slide agglutination tests.

Isolation of Staphylococcus aureus strains and determination of antimicrobial susceptibility and phage typing Various samples of *Staphylococcus aureus* were obtained to determine the efficacy of methods for *S. aureus* detection according to the art and according to the present invention. A total of 79 methicillin-resistant *S. aureus* (MRSA) strains were collected as clinical samples originating from 12 different hospitals and clinics in Finland. In order to minimize the possibility of obtaining the same bacterial strain from different patients, a period of at least three months was required between the isolation of samples originating from the same hospital or clinic. Twenty methicillin-sensitive *S. aureus* strains were collected each year (1980–1990) as controls for slide agglutination tests. All strains were stored in milk-glycerol (1 L contained 40.0 g milk powder, 140 ml glycerol, and 850 ml water) at −70° C. and cultivated on sheep blood agar plates for 20–24 hours at 37° C. prior to testing. Further, all strains were coagulase, deoxyribonuclease, and urease producers and were capable of forming acid from maltose and trehalose. Strains which gave a negative result in MRSA agglutination tests were identified as *S. aureus* by an API-Staph™ assay (Biomerieux).

Antimicrobial susceptibility of subject *S. aureus* strains was determined with Neo-sensitabs™ disks (A/S Rosco) and Mueller-Hinton II medium (BBL, Becton-Dickinson Microbiology Systems). Methicillin resistance was determined with 1 microgram oxacillin discs on Mueller-Hinton agar plates (BBL, Cockeysville, Md., a one liter plate contained 2.0 g beef extract, 17.5 g casein hydrolysate, 1.5 g starch, and 17.0 g agar) which were incubated at 30° C.

Minimal inhibitor concentration (M IC) values for oxacillin were determined by plate dilution on Mueller-Hinton II agar plates with 4% NaCl under 37° C. incubation. Strains having an MIC for oxacillin of greater than or equal to 4 micrograms/milliliter were regarded as methicillin resistant. Similar methods known to the skilled artisan may be used to determine the susceptibility of strains to other antimicrobial compounds.

Phage typing was performed using the International Phage Set according to Blair, *Bull. World. Health Org.*, 24: 771–784 (1961), incorporated by reference herein.

Susceptibility of isolated MRSA-aggl⁻ strains to various antibiotics is shown in Table 1. Strains were shown to represent five different types, consisting of two phage types (strains a, b, c, which belong to phage type 81/42E/47/54/75/84/85; and strains d and e, belonging to phage type 85, as reported in Blair, et al., *Bull. World Health Org.*, 24: 771–784 (1961)). Neither phage type was common to any strains which produced positive MRSA agglutination results.

TABLE 1

Antibiotic Resistance of MRSA-aggl⁻ Strains

| Strain | No. Isolates | Erythromycin | Clindamycin | Tobramycin |
|--------|--------------|--------------|-------------|------------|
| a | 4 | R | R | R |
| b | 1 | S | S | R |
| c | 2 | S | S | S |
| d | 2 | R | R | R |
| e | 5 | R | S | R |

In Table 1, R denotes resistance to the indicated antibiotic and S denotes sensitivity to the indicated antibiotic.

Characterization of MRSA Strains

Agglutination tests were performed by cultivating methicillin-resistant *S. aureus* strains on sheep blood agar plates overnight at 37° C. The slide agglutination test, Staphyslide-Test™ (BioMeriux), was used. That test is a hemagglutination test employing fibrinogen-coated or uncoated (control) sheep red blood cells in order to detect clumping factor on *S. aureus* (i.e., agglutination, a positive test result). Also employed were a Staphaurex™ (Wellcome Diagnostics) assay or an ANI *S. aureus* TEST™ (Ani Biotech Oy, Finland) assay, both of which are latex agglutination assays in which particles are coated with fibrinogen and immunoglobulin G in order to detect *S. aureus* clumping factor or protein A, respectively. All of the assays were conducted according to the manufacturer's instructions.

Eleven of the 79 MRSA strains obtained tested negative in the above-mentioned standard agglutination assays and three strains displayed variable results, but were included as MRSA-aggl⁻ strains. The proportion of MRSA-aggl⁻ strains thus was 17.7% (14/79, See Table 1). There was no statistically-significant difference (Student's T-test) between the MIC values for oxacillin in MRSA-aggl⁻ and positively-agglutinating cells.

Preparation of Antiserum Against MRSA-aggl⁻ Strains

Antiserum against MRSA strains which tested negative in standard agglutination tests according to the art (MRSA-aggl⁻) was prepared by immunizing rabbits with $10^9$ heat-killed MRSA-aggl⁻ bacterial cells in 0.5 ml Freund's complete adjuvant by three subcutaneous injections at two-week intervals. Ten days after the final booster injection, blood was collected by heart puncture and the serum isolated. The antiserum was absorbed twice with intact *Staphylococcus epideimidis* (ATCC Accession No. 12228), using $2 \times 10^9$ bacteria per milliliter antiserum for 2 hours at 4° C. grown on Todd-Hewitt broth (BBL, one liter contained 3.1 g beef heart infusion, 20.0 g peptone, 2.0 g dextrose, 2.0 g NaCl, 0.4 g Di-Na-phosphate, 2.5 g Na-carbonate).

EXAMPLE 1

Identification of a MRSA-aggl⁻-specific 230 Kilodalton (KDa) surface protein

MRSA strains (MRSA-aggl⁺ and aggl⁻) were subjected to lysostaphin digestion and analysis to determine the composition of membrane surface-bound proteins which might act as antigens in *S. aureus* agglutination detection assays. Strains were grown on Todd-Hewitt broth overnight at 37° C. and then collected by centrifugation and washed twice with phosphate-buffered saline (PBS). Bacterial density was adjusted to approximately $2 \times 10^{10}$ bacterial cells/ml. Digestion was accomplished by incubating 0.5 ml bacterial suspension for 2 hours at 37° C. with 10 µg recombinant lysostaphin (Applied Microbiology, New York, N.Y.), 4 µg RNAase, and 4 µg DNAase (Sigma, St. Louis, Mo.) in the presence of phenylmethylsulfonyl fluoride (Sigma) and ethylmaleimide (Sigma). Unbroken bacterial cells were removed by centrifugation and the supernatants were incubated for 15 minutes at 80° C. to inhibit enzyme activity. Finally, protein concentration in the digests was determined as reported in Lowry, et al., *J. Biol. Chem.*, 193: 265–275 (1951).

Lysostaphin digests were then run on standard SDS-PAGE using slabs containing 8% acrylamide according to a procedure described in Laemmli, *Nature*, 277: 680–685

(1970). Other SDS-PAGE procedures are known to the skilled artisan. The resulting gels were stained with Coomassie blue for protein and, when necessary, subsequently transferred electrophoretically to nitrocellulose membranes according to a procedure reported in Towbin, et al., *Proc. Nat. Acad. Sci. (USA)*, 76: 4350–4354 (1979). Membranes were pretreated for one hour at room temperature with PBS containing 5% (weight per volume) defatted milk powder and 1% (volume per volume) Triton X-100. They were then washed with TEN-Tween buffer (0.05M Tris-HCl, pH 7.5, 0.025M EDTA, 0.15M NaCl, 0.5% (volume/volume) Tween 20). The membranes were first probed with an anti-MRSA-aggI$^-$ antiserum or control serum diluted 1:200 and subsequently with horseradish peroxidase-conjugated F(ab)$'_2$ fragments of sheep anti-rabbit-IgG antibodies (Jackson ImmunoResearch), both diluted in TEN-Tween buffer. Finally, membranes were washed four times with TEN-Tween buffer and once with PBS. The resulting bands were visualized by incubating membranes in 50 ml of 50 mM acetate buffer, pH 5.0, containing 10 mg of 3-amino-9-ethylcarbazole, 2.5 ml N,N'-dimethylformamide, and 30% hydrogen peroxide (30 µl).

Figure 1A:
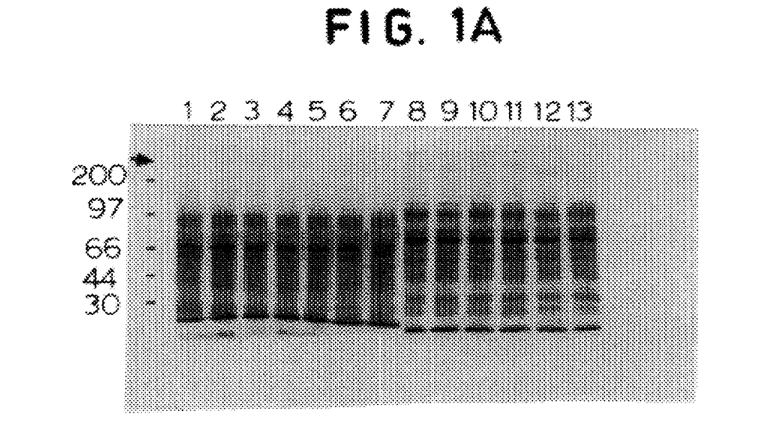
FIGS. 1A and 1B show gels obtained from SDS-PAGE analysis of lysostaphin digests of various MRSA-aggl⁻ and agglutination-positive strains, respectively, which were stained for protein.
Figure 1B:
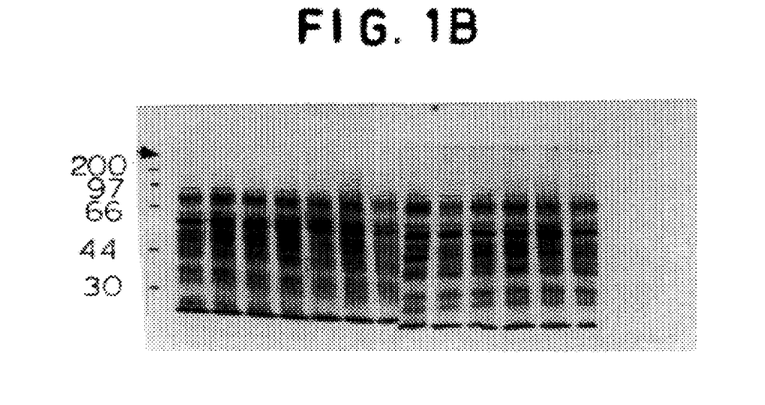
Figure 2A:
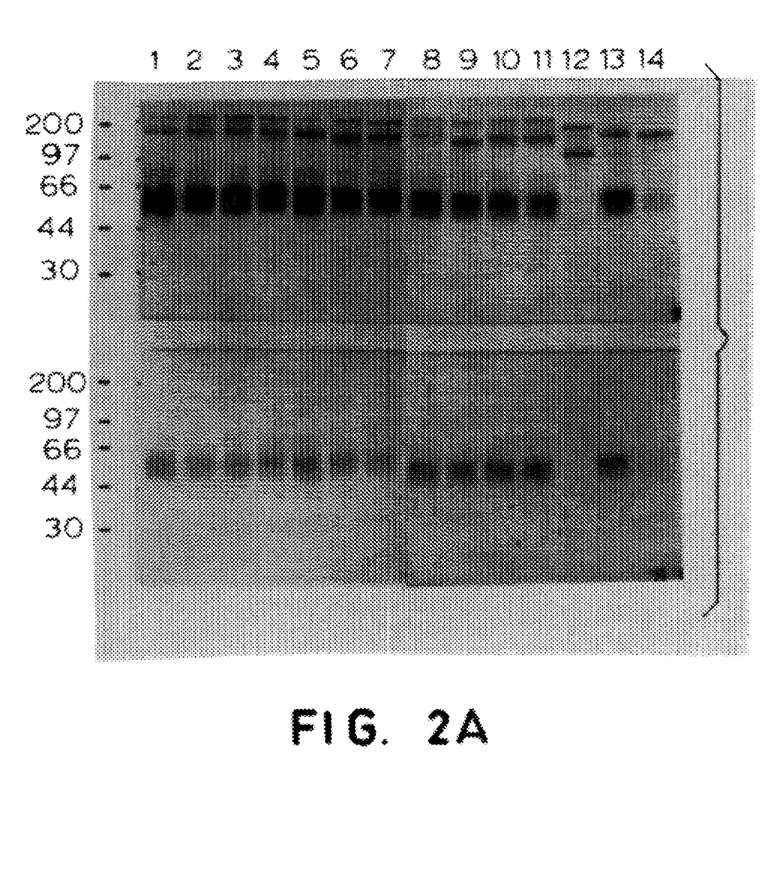
FIGS. 2A and 2B show the results of immunoblots of lysostaphin digests of MRSA-aggl⁻ strains.
Figure 2B:
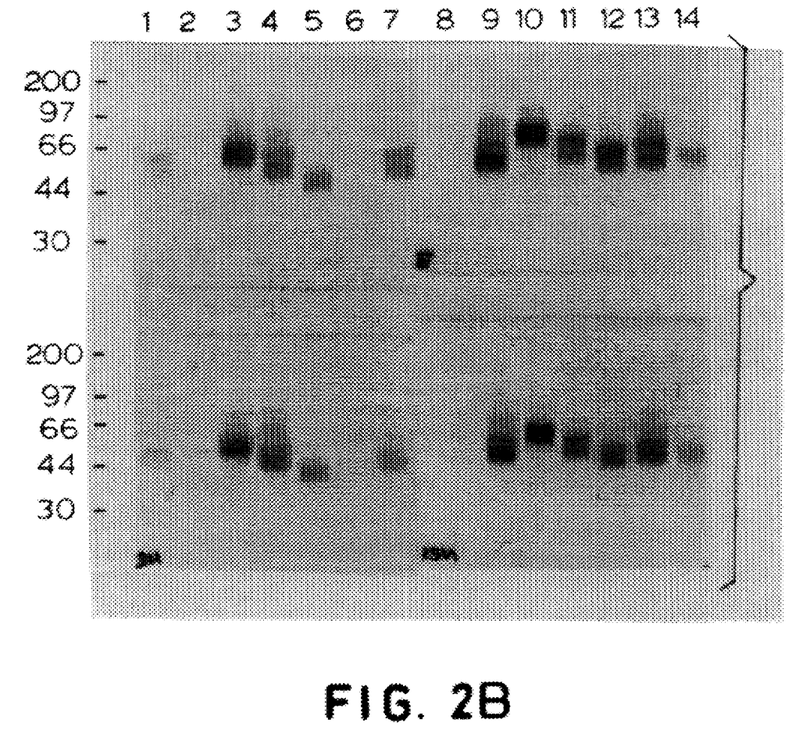

Analysis of lysostaphin digests of MRSA membrane fractions revealed that only the MRSA-aggI$^-$ strains contained a protein having an approximate molecular weight of 230 KDa. That protein was not visualized in agglutination-positive strains as shown in FIGS. 1A and 1B; wherein the arrow indicates the MRSA-230 protein (not detected in the MRSA-aggI$^+$ strains). Molecular weight markers are shown on the left of the Figures. FIG. 1A shows that digests of $^{11}/_{14}$ MRSA-aggI$^-$ strains contain an approximately 230 KDa protein band (lanes 1–11) which was not visualized in digests of agglutination-positive strains (lanes 1–14 in FIG. 1B). One MRSA-aggI$^-$ strain showed a band at approximately 195 kDa (FIG. 1A, lane 12) and in two digests, no corresponding band was evident (FIG. 1A, lanes 13 and 14).

EXAMPLE 2

Isolation of 230 KDa Protein From MRSA-aggI$^-$ Strains

The products of lysostaphin digests, which contained the MRSA-230 protein, were then 5× concentrated and purified. Purification was accomplished by first subjecting the digests to gel filtration using Sephacryl S-300 HR gel (Pharmacia Fine Chemicals) in 50 mM Na-phosphate (pH 7.4)/500 mM NaCl with 0.1 mM EDTA (ethylene diamine tetraacetic acid), 0.1 mM DTT (dithiothreitol), 0.1 mM PMSF (phenyl methyl sulfonyl fluoride), 1 mM Benzamidine, and 0.15 mM N-ethylmaleimide. Fractions (6 ml) determined on the basis of SDS-PAGE to contain the MRSA-230 protein were pooled and concentrated using partial lyophilization.

Concentrated gel filtration pools were further fractionated by ion exchange HPLC chromatography using a Mono-Q 5/5 HR column (Pharmacia) with a buffer A comprising 50 mM Tris-HCl, pH 8.0, and a buffer B comprising buffer A plus 1M NaCl, with a gradient of 0–60% of buffer B (i.e., a linear NaCl gradient from 0 to 0.6M). Fractions containing the MRSA-230 protein eluted at 420 to 580 mM NaCl and those fractions were pooled for hydrophobic interaction chromatography. The NaCl concentration was adjusted to 4.0M.

Hydrophobic interaction chromatography utilized a phenyl-Superose 5/5 HR column (Pharmacia), with a NaCl gradient from 4.0M to 0M in a buffer comprising 50 mM Na-phosphate, pH 7.0. Only the MRSA-230 protein and its degradation products (see below) were detected in the eluate under the aforestated conditions. Accordingly, the flow-through fractions contained the MRSA-230 protein.

Another protein, having an approximate molecular weight of 175 kDa, was observed in a separate flow-through fraction. That 175 kDa protein was determined to be a proteolytic degradation product of MRSA-230, because anti-MRSA-230 antibodies reacted with the 175 kDa protein. Moreover, tryptic peptide maps of purified 175 kDa protein and of a MRSA-230/175 kDa protein mixture were almost identical. The pool containing MRSA-230 was dialysed against distilled water and lyophilized by freezing to −70° C. and transferring to a room-temperature vacuum.

EXAMPLE 3

Alkylation and Tryptic Digestion of MRSA-230 to Determine Partial MRSA-230 Amino Acid Sequences The purified, lyophilized MRSA-230 protein was then reduced by first dissolving 15–20 µg aliquots of the purified fractions in 50 microliters of a solution containing 0.5M Tris-HCl, pH 7.5, 6M guanidine-HCl, and 2 mM EDTA and then immediately adding 5 µl of 1.4M DTT. The mixture was allowed to incubate for 10 minutes at 20° C. Alkylation was next performed by adding 1 µl 4-vinyl pyridine to the above mixture and incubating for 10 minutes at 20° C. By-products of the reducing and alkylating steps were then removed by reverse-phase C4 chromatography. The $C_4$ column (Vydac 214TP52, 2.1 mm×250 mm) was equilibrated with 10% (by vol.) acetonitrile, 0.1% (by vol.) trifluoroacetic acid and eluted with a linear acetonitrile gradient from 10% to 60%. The eluted proteins were collected manually. The purified alkylated MRSA-230 protein was solubilised in 50 µl 0.1M ammonium bicarbonate, pH 7.0, and digested with 0.2 microliters tosylphenylalaninechloromethane-treated trypsin (1 hour incubation at 37° C.) followed by addition of 0.5 µl trypsin (0.5 mg/ml) in 10 mM HCl and incubation overnight at 37° C.

The MRSA-230 peptide fragments produced by tryptic digestion were then characterized by high performance liquid chromatography using an Applied Biosystems 400 solvent delivery system, a 490 dynamic mixer, and 783A programmable detector on an RP Vydac 214TP52-C4 column (4.6×25 mm) according to the Manufacturer's instruction, or a $C_{18}$ column (Vydac 218TPB52, 2.1 mm×250 mm) with a linear acetonitrile gradient from 0 to 60% in 0.1% trifluoroacetic acid. Amino acid sequencing of the isolated peptides was performed in an Applied Biosystems 477A/120A pulse-liquid protein sequencer by means of Edman degradation. The tryptic digestion of purified and reduced MRSA-230 protein produced the following identifiable peptide sequence fractions of MRSA-230:

Thr-Thr-Thr-Pro-Thr-Thr-Ile-Asn (SEQ ID NO: 1)
Pro-Tyr-Ala-Xaa-Phe-Val (SEQ ID NO: 2)
Phe-Asn-Pro-Asp-Leu-Lys-Pro-Gly-Glu-Glu (SEQ ID NO: 3)
Glu/Asn-Pro/Gly-Glu-Thr-Gly-Glu-Val-Val-Thr-Pro-Pro-Val-Asp (SEQ ID NO: 4)
Ala-Leu-Ala-Ile-Ala-Gly-Ala/Val (SEQ ID NO: 5).
Gly-Glu-Pro-Glu-Val-Thr-Xaa-Glu-Glu (SEQ ID NO: 6)
Lys-Pro-Thr-Leu-Glu-Pro (SEQ ID NO: 7)
Asn-Phe-Leu-Ile-Thr (SEQ ID NO: 8)

The skilled artisan recognizes that standard techniques in the art may be used to generate a set of oligonucleotide probes, based upon the above sequence fragments, which may be used to probe a library of cDNA from methicillin-resistant *S. aureus* which do not test positive on standard slide agglutination tests in order to isolate, clone, and sequence the gene(s) encoding MRSA-230, and thereby deduce the predicted amino acid sequence of MRSA-230.

EXAMPLE 4

Characteristics of The MRSA-230 Protein

The 230 KDa protein (MRSA-230 protein) isolated as described above was analyzed by immunoblotting. Rabbits were immunized with MRSA-aggl$^-$ bearing the MRSA-230 protein and agglutination positive strains in the manner described above.

The results are shown in FIGS. 2A and 2B, wherein Molecular weight markers are provided on the left side of the Figure. Anti-MRSA-230 antibodies absorbed with *S. epidermidis* principally visualized the 230 KDa MRSA-230 protein and a 175 KDa protein, which was probably due to proteolytic degradation of the 230 KDa protein (FIG. 2A). Neither the 230 KDa nor the 175 KDa proteins were observed in digests of MRSA strains which displayed positive agglutination tests. Other minor bands were detected in immunoblots of MRSA-aggl$^-$ strains (FIG. 2A, lanes 1–11). One polypeptide band was visualized with control serum (FIG. 2B) but control serum produced no bands in the region of the 230 KDa protein or its suspected degradation products.

EXAMPLE 5

Direct Agglutination Assay Using Anti-MRSA-230 Antibodies

Direct agglutination assays, as provided above, were performed in which rabbit antiserum was obtained by immunization with MRSA-aggl$^-$ strains absorbed with *S. epidermidis* and with purified anti-MRSA-230 antibodies. Anti-MRSA-230 antibodies were purified from antiserum conventionally, by adsorbing the antibodies to nitrocellulose membranes to which the MRSA-230 protein was bound. After washings with phosphate-buffered saline (PBS), the anti-MRSA-230 antibodies were eluted by incubating the membranes for 10 min. in 1.0M acetate, pH 2.0. The eluate was then neutralized and concentrated.

Direct bacterial agglutination assays were performed by mixing 2–3 colonies of Staphylococci with absorbed and 1:7 diluted anti-MRSA-aggl$^-$ antiserum or with concentrated purified anti-MRSA-230 antibodies on a coverslip. Agglutination was recorded after 10–30 seconds. Serum from nonimmunized rabbits was used as a control.

The results are summarized in Table 2. As shown, anti-MRSA-aggl$^-$ antiserum detected all the MRSA-aggl$^-$ strains and 64/65 agglutination-positive strains. None of 52 *S. epidermidis* strains also tested were detected as positive, even though they were all methicillin-resistant. In a separate test, purified anti-MRSA-230 antibodies detected all 14 MRSA-aggl$^-$ strains. These results show that anti-MRSA-230 antibodies detect methicillin-resistant strains of *S. aureus* with high specificity and, further, that anti-MRSA-230 antibodies, or serum containing them, detects methicillin-resistant *S. aureus* strains not detected by standard methods (see above).

TABLE 2

Direct Agglutination Assay

| Strain | No. | Agglutination Antiserum: anti-MRSA-aggl$^-$ | anti-230 | NRS |
|---|---|---|---|---|
| MSSA | 32 | 20 | NT | 0 |
| MRSA-aggl$^-$ | 14 | 14 | 14 | 0 |
| MRSA-aggl$^+$ | 65 | 64 | 0 | 0 |
| *S. epidermidis* | 52 | 0 | NT | 0 |
| Coagulase Neg. Staphylococci | 16 | 1 | NT | 0 |

In Table 2, MRSA-aggl$^+$ indicates strains which tested positive for *S. aureus* in standard slide agglutination tests; NT designates antisera not tested, and MSSA designates strains which were methicillin-sensitive *S. aureus*. These results demonstrate that anti-MRSA-230 antibodies specifically detect those methicillin-resistant strains of *S. aureus* which were not detected (i.e., gave false negative results) in conventional slide agglutination assays and that anti-MRSA-aggl$^-$ antiserum detects nearly all strains of *S. aureus*, whether or not such strains produce positive results in standard slide agglutination test.

The MRSA-230 protein is a unique *S. aureus* protein and appears not to be related to other known protein factors in *S. aureus*. Other cell surface proteins, such as the 48 kDa pentaglycine cross-linking protein and the 74 kDa penicillin-binding protein have molecular weights considerably lower than MRSA-230. Accordingly, the MRSA-230 is a unique marker for *S. aureus* and effectively detects methicillin-resistant strains when standards assays of the art do not.

EXAMPLE 6

Rapid MRSA-230 Purification Using Plant Lectin Affinity Chromatography

As set forth in detail below, carbohydrate analysis unexpectedly indicated that MRSA-230 is a glycoprotein. It was further determined that a high affinity of the MRSA-230 glycoprotein for certain plant lectins provided a rapid and efficient method of MRSA-230 purification.

Lysostaphin digests of non-agglutinating, methicillin-resistant *S. aureus* were conducted. Staphylococci grown in 1 liter Todd-Hewitt medium were suspended in 20 ml NaCl/$P_i$ (0.5M sodium phosphate, pH 7.4, 0.14M sodium chloride) containing 20 micrograms of lysostaphin, 16 micrograms DNase, 16 micrograms RNase, 10 mM phenylmethylsulfonyl fluoride (PMSF), 24 mg N-ethylmaleimide, and incubated for 2 hours at 37° C. The bacteria were removed by centrifugation (12000×g, 10 min., 4° C.). The reaction was stopped by heating the suspension for 15 min. at 80° C. and the lysate was used immediately or stored at −20° C. The lysate, which contained the solubilized MRSA-230 protein, was clarified by centrifugation (10000×g, 10 min., 4° C.).

The soluble fraction of lysostaphin digests were analyzed via SDS-PAGE. Staining with Coomassie brilliant blue revealed a multiplicity of *S. aureus* proteins, whereas only MRSA-230 protein and the 175 kDa fragment thereof were observed following staining with periodate/Schiff's reagent to identify glycoproteins.

To further characterize the observed carbohydrate component of MRSA-230, interactions between MRSA-230 protein and various lectins were studied by means of ligand-blotting and a modified ELISA technique. For ligand-blotting, the purified MRSA-230 protein was transferred to nitrocellulose filters which were blocked with 0.5M sodium phosphate, pH 7.4, 0.14M sodium chloride (NaCl/$P_i$) containing 5% bovine serum albumin (BSA) and probed with various FITC-conjugated or TRITC-conjugated lectins in NaCl/$P_i$ containing 0.1% BSA. Interactions with lectins were detected under ultraviolet light.

For ELISA, wells were coated with various concentrations of the purified protein in sodium carbonate, pH 9.6, overnight at 4° C. The wells were washed three times with 0.05% (by vol.) Tween 20 and blocked with NaCl/$P_i$ containing 1% BSA for 1 h at 20° C. The wells were treated with HRP-WGA or HRP-HPA1 (10 micrograms/ml in NaCl/$P_i$ containing 1% BSA) for 1 hour at 20° C. in the absence or presence of an inhibitor. After washing with NaCl/$P_i$, substrate solution (0.2 mg 1,2-phenylenediamine dihydrochloride/1 ml sodium citrate, pH 5.0) was added. The reaction was stopped with 12.5% sulfuric acid and the absorbance was recorded at 492nm.

Lectins included in the affinity studies included fluorescein isothiocyanate (FITC)-conjugated lectins from Helix-pomatia (HPA I) Triticum vulgaris (wheat germ agglutinin, WGA). Wistaria floribunda, Ricinus communis and Arachis hypogaea; and horseradish peroxidase (HRP)-conjugated HPA I and WGA (EY Labs. Inc.); FITC-conjugated Jacalin (Kem-En-Tek); and tetramethylrhodamine isothiocyanate (TRITC)-conjugated lectin from Glycine max (Vector Laboratories).

In the ligand-blotting experiments, HPA I and WGA bound to the 230/175-kDA protein. Only WGA showed binding in the ELISA. None of the other lectins tested (i.e., Jacalin or lectins from W. floribunda, R. communis, A. hypogaea or G. max) bound the 230/175-kDa protein. Glucose and N-acetylglucosamine inhibited the binding of WGA by 40% and 92%, respectively.

The affinity of certain plant lectins for MRSA-230 protein was advantageously employed in a MRSA-230 purification protocol. From the lectin studies described above, affinity chromatography using WGA-Sepharose (Pharmacia) was selected. Ten to 100 ml of lysostaphin digest was incubated with 5–10 ml WGA-Sepharose for 1 hour at 4° C. The particles were packed into a column, washed with NaCl/$P_i$, and eluted with 100 mM N-acetylglucosamine. Fractions of 0.25–1.0 ml were collected. Fractions that contained the protein were pooled and the sugar was removed by gel filtration on PD-10 columns (Pharmacia) equilibrated in NaCl/$P_i$.

This single-step purification method (affinity chromatography using WGA-Sepharose) proved to be very efficient. SDS/PAGE analysis (Coomassie blue staining) of the material that eluted with 100 mM N-acetylglucosamine revealed only the 230-kDA and 175-kDa proteins.

EXAMPLE 7

Demonstration of Vaccine Properties of MRSA-230 Protein

The following procedures are performed to demonstrate the vaccine properties (i.e., the ability to confer protective immunity) of a composition comprising MRSA-230 protein or biologically active fragments thereof.

Four groups (A, B, C, and D) of animals are employed in the procedure. Experimental groups A and B are immunized with a composition containing purified MRSA-230 protein or biologically active fragments thereof. Preferred compositions contain, in addition to the MRSA-230 protein, an adjuvant such as Freund's complete adjuvant. Control groups C and D are immunized with a similar composition, except that a control S. aureus protein is substituted for the MRSA-230 component. Exemplary control proteins include purified protein A and fibronectin binding protein. Exemplary immunization schedules are as follows:

Groups A and C: Immunize one time; challenge with S. aureus bacteria one week after immunization;

Groups B and D: Immunize three times at two week intervals; challenge with S. aureus bacteria one week after third immunization. Vaccine properties of MRSA-230 protein or biologically active fragments thereof are demonstrated where an experimental group of animals is observed to suffer fewer infections and/or less severe infections compared to the corresponding control group.

One preferred animal model for the foregoing experiments is a mouse bacteremia and renal abscess model. Mice (C57BL/6J; Jackson Laboratories, Bar Harbor, Me., USA)) are inoculated intravenously with sublethal does of S. aureus cells. The bacterial growth in blood is monitored daily by determining colony forming units in a blood sample. On day 7 the animals are killed, kidneys excised, homogenized, and quantitatively cultured.

Another preferred animal model is a mouse endocarditais model. Injury to the aortic valves is first caused by insertion of a catheter via the jugular vein of the mice. Bacterial challenge is performed by innoculating the mice intravenously. S. aureus growth in blood is monitored daily by determining colony forming units in a blood sample. On day 6 the mice are killed and the heart valves excised, homogenized, and quantitatively cultured.

Other suitable animal models, immunization schedules, and the like will be apparent to those of ordinary skill.

Further Characterization of MRSA-230 Protein and its role in the non-agglutinating phenotype Staphylococcal surface proteins were labelled by means of the Iodogen method. See Kuusela & Saksela, Eur. J.Biochem., 193: 759–765 (1990). $2 \times 10^{10}$ S. aureus cells in 300 microliters NaCl/$P_i$ were incubated in an Iodo-gen-coated tube with 0.5 mCi Na$^{125}$I for 10 min. at 0° C. The cells were pelleted by centrifugation and washed six times with 1.0 ml NaCl/$P_i$. The bacteria were suspended in 500 microliters of NaCl/$P_i$ and treated with lysostaphin essentially as described above. The lysostaphin digest was lyophilized, dissolved in 100 microliters of distilled water, and analyzed by SDS/PAGE and autoradiography on Kodak X-Omat film.

Protease studies of MRSA-230 were also conducted, involving digestion of bacteria with exogenous trypsin, plasmin, and surface-associated plasmin. $2 \times 10^9$ staphylococci in 100 microliters NaCl/$P_i$ were digested with 15 micrograms trypsin at 37° C. and 50 microliter samples were taken at time points ranging from 15 to 240 minutes. The bacteria were collected by rapid centrifugation, washed twice with ice-cold NaCl/$P_i$ containing 1 mM PMSF, suspended in the same buffer and treated with lysostaphin as described above. After lysostaphin treatment, the lysates were collected by centrifugation and analyzed by SDS/PAGE.

For adherence studies, $10^{10}$ staphylococci in 1 ml NaCl/$P_i$ were digested with 3 micrograms of plasmin at 20° C. for 30 min. Bacteria were collected by centrifugation, washed twice with NaCl/$P_i$ containing 0.1 mM PMSF and aprotinin (2 micrograms/ml) and suspended in NaCl/$P_i$ containing 1% BSA to a cell density of $2 \times 10^{10}$ bacteria/ml. Surface-associated plasmin was generated by methods described in the art. See Kuusela & Saksela, supra; Kuuscla, et al., *Infec. Immmun.*, 60, 196–201 (1992). $2 \times 10^{10}$ staphylococci were incubated in 1 ml NaCl/$P_i$ containing 10 micrograms tissue-type plasminogen activator, 20 micrograms plasminogen and 5 micrograms $\alpha_2$-antiplasmin for 2 hours at 20° C. The bacteria were collected by centrifugation and washed twice with ice-cold NaCl/$P_i$. The presence of functionally active plasmin on the staphylococcal surface (or in the supernatant) was monitored with a chromogenic substrate, D-valyl-L-leucyl-Llysyl-p-nitroanilide hydrochloride. See Kuusela & Saksela (1990). After generation of the surface-associated plasmin, the bacteria were treated with lysostaphin as described above, and analyzed by SDS/PAGE.

Treatment of the intact MRSA-aggl⁻ bacteria with exogenous trypsin and plasmin resulted in rapid conversion of the 230-kDa MRSA-230 protein to the 175-kDa form. Other *S. aureus* surface proteins remained intact.

Surface-associated plasmin was generated to test its effect on the 230-kDa MRSA-230 protein by incubation of the bacteria in the presence of plasminogen, tissue-type plasminogen activator and $\alpha_2$-antiplasmin. $\alpha_2$-Antiplasmin inactivates soluble plasmin but not surface-associated plasmin. The surface-associated plasmin degraded the 230-kDa protein with kinetics similar to those for degradation obtained by exogenous trypsin and plasmin. Most other *S. aureus* surface proteins remained intact except approximately 86-kDa proteins, which were equally sensitive to surface-associated plasmin. The $\alpha_2$-antiplasmin experiments demonstrated that proteolytic degradation was due to receptor-bound plasmii and not soluble plasmin.

The effects of proteolytic degradation of MRSA-230 on the ability to detect MRSA-aggl⁻ strains using conventional agglutination assays also was studied. Adhesion tests on coverslips coated with standard the ligands fibronectin, fibrinogen, IgG, and BSA showed that brief treatment of the non-agglutinrating methicillin-resistant *S. aureus* bacteria with exogenous plasmin enhanced the binding to fibronectin and IgG more than two-fold and to fibrinogen more than 20-fold. Similar results were obtained using the surface-associated plasmin instead of exogenous plasmin. This data provides a modification to standard *S. aureus* agglutination assays (e.g., the addition of a proteolysis step) to increase their sensitivity. Such modified standard agglutination assays are an additional aspect of the invention.

Although the present invention has been described in terms of preferred embodiments thereof, the skilled artisan realizes that variations and improvements will Occur to those of ordinary skill in the art upon consideration of the present invention. Therefore, it is intended that the appended claims embrace such variations and improvements and that only such limitations as are contained in the following claims should be read into the present invention.

---

What is claimed is:

1. A pharmaceutical composition comprising an antibody that specifically binds MRSA-230 in a pharmaceutically-acceptable carrier.

2. A purified antibody that specifically binds to MRSA-230 protein.

3. A purified antiserum comprising antibodies that specifically bind with an MRSA-230 protein or with a biologically active fragment thereof wherein said antiserum is obtained by a process comprising the steps of:

(a) immunizing a non-human mammal with a composition comprising at least one material selected from the group consisting of purified MRSA-230 protein biologically active fragments of MRSA-230 protein *Staphylococcus aureus* bacteria that express MRSA-230 protein, and cell membranes of *Staphylococcus aureus* bacteria that express MRSA-230 protein; and   (b) purifying antiserum from said non-human mammal, said antiserum comprising antibodies that specifically bind with an MRSA-230 protein or with a biologically active fragment thereof.

4. A kit for the detection of *Staphylococcus aureus* comprising purified antiserum according to claim 3.

5. Purified antibodies that specifically bind with an MRSA-230 protein or with a biologically active fragment thereof.

6. A kit for the detection of *Staphylococcus aureus* comprising purified antibodies according to claim 5.

7. A composition comprising purified polyclonal antibodies that specifically bind with an MRSA-230 protein or with a biologically active fragment thereof.

8. A kit for the detection of *Staphylococcus aureus* comprising a composition according to claim 7.

9. A purified antiserum comprising antibodies that specifically bind with an MRSA-230 protein or with a biologically active fragment thereof, wherein said antiserum is obtained by a process comprising the steps of:

(a) immunizing a mammal with a composition comprising a purified MRSA-230 protein or a biologically active fragment thereof; and   (b) purifying antiserum from said mammal, said antiserum comprising antibodies that specifically bind with an MRSA-230 protein or with a biologically fragment thereof.

10. A kit for the detection of *Staphylococcus aureus* comprising purified antiserum according to claim 9.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:1:

Thr Thr Thr Pro Thr Thr Ile Asn
1                     5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:2:

Pro Tyr Ala Xaa Phe Val
1                 5

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Phe Asn Pro Asp Leu Lys Pro Gly Glu Glu
 1               5                    10

( 2 ) INFORMATION FOR SEQ ID NO:4:

( i ) SEQUENCE CHARACTERISTICS:
        ( A ) LENGTH: 13 amino acids
        ( B ) TYPE: amino acid
        ( D ) TOPOLOGY: linear     ( i i ) MOLECULE TYPE: peptide     ( i x ) FEATURE:
        ( A ) NAME/KEY: misc_feature
        ( D ) OTHER INFORMATION:
            / note= "The amino acid at position 1 is
            Glycine or Asparagine."

( i x ) FEATURE:
        ( A ) NAME/KEY: misc_feature
        ( D ) OTHER INFORMATION:
            / note= "The amino acid at position 2 is
            Proline or Glycine."

( x i ) SEQUENCE DESCRIPTION: SEQ ID NO:4:

Xaa Xaa Glu Thr Gly Glu Val Val Thr Pro Pro Val Asp
 1               5                    10

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( D ) TOPOLOGY: linear     ( i i ) MOLECULE TYPE: peptide     ( i x ) FEATURE:
        ( A ) NAME/KEY: misc_feature
        ( D ) OTHER INFORMATION:
            / note= "The amino acid at position 7 is
            Alanine or Valine."

( x i ) SEQUENCE DESCRIPTION: SEQ ID NO:5:

Ala Leu Ala Ile Ala Gly Xaa
 1               5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( D ) TOPOLOGY: linear     ( i i ) MOLECULE TYPE: peptide     ( x i ) SEQUENCE DESCRIPTION: SEQ ID NO:6:

Gly Glu Pro Glu Val Thr Xaa Glu Glu
 1               5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear     ( i i ) MOLECULE TYPE: peptide (xi) SEQUENCE DESCRIPTION: SEQ ID NO:7:

Lys Pro Thr Leu Glu Pro
 1               5

(2) INFORMATION FOR SEQ ID NO:8:

(i) SEQUENCE CHARACTERISTICS:
      (A) LENGTH: 5 amino acids
      (B) TYPE: amino acid
      (D) TOPOLOGY: linear    (ii) MOLECULE TYPE: peptide    (xi) SEQUENCE DESCRIPTION: SEQ ID NO:8:

Asn Phe Leu Ile Thr
 1               5